US010105063B2

(12) United States Patent
Hirota et al.

(10) Patent No.: US 10,105,063 B2
(45) Date of Patent: *Oct. 23, 2018

(54) PHOTOACOUSTIC MEASUREMENT DEVICE AND LASER LIGHT SOURCE

(71) Applicant: FUJIFILM Corporation, Tokyo (JP)

(72) Inventors: Kazuhiro Hirota, Ashigarakami-gun (JP); Tadashi Kasamatsu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/655,097

(22) Filed: Jul. 20, 2017

(65) Prior Publication Data

US 2017/0319078 A1  Nov. 9, 2017

Related U.S. Application Data

(63) Continuation of application No. 14/801,533, filed on Jul. 16, 2015, now Pat. No. 9,743,840, which is a
(Continued)

(30) Foreign Application Priority Data

Mar. 25, 2013  (JP) .................. 2013-061502

(51) Int. Cl.
*A61B 5/00* (2006.01)
*H01S 3/06* (2006.01)
(Continued)

(52) U.S. Cl.
CPC ....... *A61B 5/0095* (2013.01); *G01N 29/0654* (2013.01); *G01N 29/2418* (2013.01);
(Continued)

(58) Field of Classification Search
CPC ............. A61B 5/0095; G01N 29/0654; G01N 29/2418; G01N 29/44; G02B 26/04;
(Continued)

(56) References Cited

U.S. PATENT DOCUMENTS 6,038,241 A   3/2000  von Elm et al.
8,761,225 B2  6/2014  Ichihara
(Continued)

FOREIGN PATENT DOCUMENTS

JP  11-224968 A   8/1999
JP  2003-17787 A  1/2003
(Continued)

OTHER PUBLICATIONS

International Search Report issued in PCT/JP2014/057064, dated Apr. 8, 2014.
(Continued)

*Primary Examiner* — Son Le
*Assistant Examiner* — David Z Huang
(74) *Attorney, Agent, or Firm* — Birch, Stewart, Kolasch & Birch, LLP

(57) ABSTRACT

A flash lamp 32 excites a laser rod 31. A Q switch 35 which changes the loss of the optical resonator according to the voltage applied is inserted on the optical path of a pair of mirrors 33 and 34 forming the optical resonator. An optical path shutter 39 is provided on the optical path of laser emission light. In a first operation mode in which laser emission is performed, the optical path shutter 39 is opened and the voltage applied to the Q switch 35 is changed from a high voltage to, for example, 0 V to emit pulsed laser light after the flash lamp 32 excites the laser rod 31. In a second operation mode in which the laser emission is interrupted and waited for, the optical path shutter 39 is closed and the voltage applied to the Q switch 35 is, for example, 0 V.

20 Claims, 4 Drawing Sheets

Related U.S. Application Data continuation of application No. PCT/JP2014/057064, filed on Mar. 17, 2014.

(51) Int. Cl.
| | |
|---|---|
| *H01S 3/00* | (2006.01) |
| *H01S 3/092* | (2006.01) |
| *H01S 3/115* | (2006.01) |
| *G01N 29/44* | (2006.01) |
| *G01N 29/24* | (2006.01) |
| *G02B 26/04* | (2006.01) |
| *G01N 29/06* | (2006.01) |

(52) U.S. Cl.
CPC .............. *G01N 29/44* (2013.01); *G02B 26/04* (2013.01); *H01S 3/005* (2013.01); *H01S 3/061* (2013.01); *H01S 3/092* (2013.01); *H01S 3/115* (2013.01); *G01N 2291/0289* (2013.01); *G01N 2291/10* (2013.01)

(58) Field of Classification Search
CPC .......... H01S 3/005; H01S 3/061; H01S 3/092; H01S 3/115
See application file for complete search history.

(56) References Cited

U.S. PATENT DOCUMENTS

| | | | |
|---|---|---|---|
| 2003/0187319 A1 | 10/2003 | Kaneko et al. | |
| 2006/0184042 A1 | 8/2006 | Wang et al. | |
| 2006/0289411 A1* | 12/2006 | Chang | B23K 26/0622 219/121.73 |
| 2011/0075688 A1 | 3/2011 | Chiang et al. | |
| 2012/0302865 A1 | 11/2012 | Tokita et al. | |
| 2013/0070802 A1 | 3/2013 | Ichihara | |

FOREIGN PATENT DOCUMENTS

| | | |
|---|---|---|
| JP | 2011-224205 A | 11/2011 |
| JP | 2012-173246 A | 9/2012 |
| JP | 2013-4851 A | 1/2013 |

OTHER PUBLICATIONS

Written Opinion of the International Searching Authority issued in PCT/JP2014/057064, dated Apr. 8, 2014.
Japanese Office Action and English translation thereof dated Jun. 13, 2017 for Application No. 2016-097719.
Japanese Office Action and English translation thereof, dated Apr. 4, 2017, for Japanese Application No. 2016-097719.

* cited by examiner

PHOTOACOUSTIC MEASUREMENT DEVICE AND LASER LIGHT SOURCE

CROSS-REFERENCE TO RELATED APPLICATIONS

This application is a Continuation of copending U.S. application Ser. No. 14/801,533, filed on Jul. 16, 2015, which is a Continuation of PCT International Application No. PCT/JP2014/057064 filed on Mar. 17, 2014, which claims priority under 35 U.S.C § 119 (a) to Japanese Patent Application No. 2013-061502 filed on Mar. 25, 2013. Each of the above applications is hereby expressly incorporated by reference, in its entirety, into the present application.

BACKGROUND OF THE INVENTION

1. Field of the Invention

The present invention relates to a photoacoustic measurement device, and more particularly, to a photoacoustic measurement device that detects photoacoustic waves generated in a subject after light is emitted to the subject. In addition, the invention relates to a laser light source used in the photoacoustic measurement device.

2. Description of the Related Art

An ultrasonic inspection method has been known as a kind of an image inspection method which can non-invasively inspect the inside of a living body. In ultrasonic inspection, a probe which can transmit and receive ultrasonic waves is used. When ultrasonic waves are transmitted from the probe to the subject (living body), the ultrasonic waves are propagated through the living body and are reflected from a tissue interface. The probe receives the reflected sound waves and a distance is calculated on the basis of the time required for the reflected ultrasonic waves to return to the probe. In this way, it is possible to image the internal structure of the living body.

In addition, photoacoustic imaging has been known which images the inside of a living body using a photoacoustic effect. In general, in this photoacoustic imaging, the living body is irradiated with pulsed laser light. In the inside of the living body, the tissue of the living body absorbs the energy of the pulsed laser light and ultrasonic waves (photoacoustic signal) are generated by adiabatic expansion caused by the energy. The photoacoustic signal is detected by, for example, a probe and a photoacoustic image is formed on the basis of the detected signal. It is possible to visualize the inside of the living body on the basis of the photoacoustic signal.

In the photoacoustic imaging, in many cases, a Q switch laser is used as a light source for emitting pulsed laser light. In the Q switch laser, a Q switch for controlling optical loss is provided in an optical resonator. For example, a Pockels cell is used as the Q switch. Until a laser medium is sufficiently excited, the Q switch is turned off to increase the loss of the optical resonator, thereby suppressing oscillation. When the Q switch is switched from the off state to an on state after the laser medium is sufficiently excited, a sufficient amount of stored energy oscillates at one time and a giant pulse which has very high intensity and a short pulse width is obtained. The Q switch returns to the off state after the pulsed laser light is emitted.

For example, JP2011-224205A discloses a photoacoustic image generation device using a Q switch laser. In JP2011-224205A, plates for pressing a subject, a detector for detecting photoacoustic waves, and a Q switch laser serving as a light source are provided in an exterior cover for shielding light. A door for manual operation is provided in the exterior cover. An operator, such as a doctor, puts a hand through the door for manual operation and interposes the subject between the plates. After the subject is interposed between the plates, light is radiated to the subject and photoacoustic waves generated in the subject are detected.

In addition, JP2011-224205A discloses a structure in which, when the door for manual operation is opened, it is determined whether to stop the emission of light from the Q switch laser or to shield laser light. When a door opening and closing detection sensor detects that the door for manual operation is opened, a control unit turns off the Q switch of the Q switch laser. In addition, the control unit closes a shutter which is provided on the optical path of the laser light such that the laser light emitted from the Q switch laser is not radiated to the subject. JP2011-224205A also discloses that it is preferable to turn off the Q switch and to close the shutter in order to further improve safety.

SUMMARY OF THE INVENTION

Here, for example, it is considered that the photoacoustic image generation device is generally used in the following situations: the number of times the photoacoustic image is continuously observed for a long time is small; and the photoacoustic image is observed in a short time before and after a surgical operation. When the photoacoustic image generation device is in a standby mode without generating the photoacoustic image, it is not necessary to emit laser light from the laser light source. However, when the excitation is stopped, the temperature of a laser rod is likely to be changed, which results in a change in light emission conditions. Therefore, it is preferable that, even in the standby mode, for example, the flash lamp is continuously turned on to periodically excite the laser medium. Since the excitation is not stopped, it is possible to constantly maintain the temperature of the laser medium. In this case, when the Q switch is maintained in an off state, it is possible to prevent laser light from being output to the outside.

However, the usage patterns of the Q switch include a pattern (first pattern) in which the Q switch is turned on to function as a quarter-wave plate and is turned off to transmit light, without changing a polarized state, and a pattern (second form) in which the Q switch is turned off to function as the quarter-wave plate and is turned on to transmit light, without changing a polarized state. In the first pattern, no voltage is applied to the Q switch until the excitation is completed and a high-voltage pulse of, for example, about 3 kV is applied to the Q switch at the emission time of pulsed laser light. The level of the applied voltage is determined by the material forming the Pockels cell used and the wavelength. In the second pattern, a high voltage of about 3 kV is continuously applied to the Q switch until the excitation is completed and the voltage applied to the Q switch is reduced to 0 V at the emission time of the pulsed laser light (negative pulse).

In the first pattern, when no voltage is applied to the Q switch, the Q switch is turned off. Therefore, when the device waits for light emission while continuously performing excitation, it is not necessary to continuously apply a high voltage to the Q switch. However, when the Q switch transmits light without changing the polarized state, it is necessary to provide a separate quarter-wave plate in the optical resonator in order to increase the optical loss of the optical resonator. In contrast, in the second pattern, it is not necessary to provide a quarter-wave plate in the optical resonator and it is possible to simplify the structure of the optical resonator and thus reduce the size or costs of the device. However, in the second pattern, when only excitation is performed with the Q switch turned off, it is necessary to continuously apply a high voltage to the Q switch. When a high voltage is continuously applied to the Q switch, the Q switch deteriorates.

In JP2011-224205A, when the door for manual operation is opened, the Q switch is turned off in order to stop the emission of laser light. In the second pattern, when the Q switch is used, it is possible to continuously apply a high voltage to the Q switch. JP2011-224205A also discloses a structure in which the shutter is closed to shield laser light. In this case, the Q switch is controlled by the same method as that used for general laser emission. Therefore, a high voltage needs to be continuously applied to the Q switch except for during a short time for which the Q switch is turned on. Therefore, JP2011-224205A does not disclose means for solving the above-mentioned problems.

The invention has been made in view of the above-mentioned problems and an object of the invention is to provide a photoacoustic measurement device and a laser light source which can simplify the structure of an optical resonator and suppress deterioration of a Q switch even when a waiting time for which no light is emitted is long.

In order to achieve the object, according to the invention, there is provided a photoacoustic measurement device including: a laser light source; an acoustic wave detection unit that, after light is emitted from the laser light source to a subject, detects a photoacoustic wave generated by the emission of the light; and a photoacoustic signal processing unit that performs signal processing for the photoacoustic wave. The laser light source includes: a laser medium; an excitation unit that excites the laser medium; an optical resonator including a pair of mirrors that face each other with the laser medium interposed therebetween; a Q switch that is provided on an optical path of the optical resonator and changes optical loss of the optical resonator, according to a voltage applied, such that the optical loss of the optical resonator when a first voltage is applied to the Q switch is more than the optical loss of the optical resonator when a second voltage lower than the first voltage is applied to the Q switch; and an optical path shutter that is provided on an optical path of laser emission light and switches between the transmission and blocking of the laser emission light. In a first operation mode in which laser emission is performed, the optical path shutter transmits the light from the laser light source and the voltage applied to the Q switch is changed from the first voltage to the second voltage to emit pulsed laser light after the excitation unit excites the laser medium. In a second operation mode in which the laser emission is interrupted and waited for, the optical path shutter blocks the light from the laser light source and the second voltage is applied to the Q switch.

In the photoacoustic measurement device according to the invention, in the second operation mode, the excitation unit may periodically excite the laser medium.

The second voltage may be 0 V.

The Q switch may cause a predetermined phase difference between a polarized component which is parallel to an optical axis of transmitted light and a polarized component which is perpendicular to the optical axis when the first voltage is applied and may not cause a phase difference between the polarized component which is parallel to the optical axis of the transmitted light and the polarized component which is perpendicular to the optical axis when the second voltage is applied.

The Q switch may function as a quarter-wave plate for light with a wavelength of laser light when the first voltage is applied.

The photoacoustic signal processing unit may generate a photoacoustic image on the basis of a photoacoustic signal.

The laser light source may further have an interrupter closing detector that detects the closing of the optical path shutter. In this case, when the interrupter closing detector detects that the optical path shutter is closed, the voltage applied to the Q switch may be controlled to be the second voltage.

When an instruction to measure a photoacoustic signal is input, the photoacoustic measurement device may operate in the first operation mode. When an instruction to stop the measurement of the photoacoustic signal is input, the photoacoustic measurement device may operate in the second operation mode.

According to the invention, there is provided a laser light source including: a laser medium; an excitation unit that excites the laser medium; an optical resonator including a pair of mirrors that face each other with the laser medium interposed therebetween; a Q switch that is provided on an optical path of the optical resonator and changes optical loss of the optical resonator, according to a voltage applied, such that the optical loss of the optical resonator when a first voltage is applied to the Q switch is more than the optical loss of the optical resonator when a second voltage lower than the first voltage is applied to the Q switch; and an optical path shutter that is provided on an optical path of laser emission light and switches the transmission and blocking of the laser emission light. In a first operation mode in which laser emission is performed, the optical path shutter transmits the light from the laser light source and the voltage applied to the Q switch is changed from the first voltage to the second voltage to emit pulsed laser light after the excitation unit excites the laser medium. In a second operation mode in which the laser emission is interrupted and waited for, the optical path shutter blocks the light from the laser light source and the second voltage is applied to the Q switch.

In the photoacoustic measurement device according to the invention, when the first voltage, which is a high voltage, is applied, the Q switch inserted into the resonator increases the optical loss of the optical resonator. When the second voltage, which is a low voltage, is applied, the Q switch decreases the optical loss of the optical resonator. The optical path shutter is provided on the optical path of laser emission light. In the second operation mode in which laser emission is interrupted and the laser emission is waited for, the optical path shutter is closed and the second voltage, which is a low voltage, is applied to the Q switch. In the second operation mode, when the excitation unit excites the laser medium, laser oscillation that is weaker than Q switch oscillation occurs in the optical resonator since the second voltage, which is a low voltage, is applied to the Q switch. However, since the optical path shutter is closed, oscillation light is prevented from being emitted prior to the optical path shutter. According to this structure, it is not necessary to continuously apply a high voltage to the Q switch in order to prevent the emission of light even when the waiting time for which no light is emitted is long and it is possible to suppress deterioration of the Q switch. In addition, since a separate quarter-wave plate does not need to be provided in the optical resonator, it is possible to simplify the structure of the optical resonator.

DESCRIPTION OF THE PREFERRED EMBODIMENTS

Figure 1:
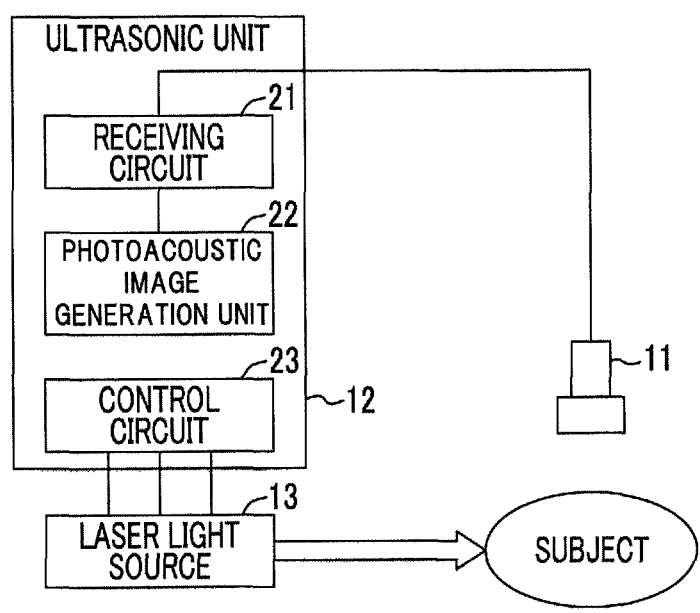
FIG. 1 is a block diagram illustrating a photoacoustic measurement device according to a first embodiment of the invention.

Hereinafter, embodiments of the invention will be described in detail with reference to the drawings. FIG. 1 illustrates a photoacoustic measurement device according to a first embodiment of the invention. A photoacoustic measurement device 10 includes an ultrasonic probe (probe) 11, an ultrasonic unit 12, and a laser light source unit 13. In the embodiment of the invention, ultrasonic waves are used as photoacoustic waves. However, the photoacoustic waves are not limited to the ultrasonic waves. For example, acoustic waves with an audio frequency may be used as long as an appropriate frequency can be selected according to a subject or measurement conditions.

The laser light source unit 13 emits pulsed laser light to be radiated to the subject. The laser light emitted from the laser light source unit 13 is guided to the probe 11 by a light guide unit, such as an optical fiber, and is then radiated from the probe 11 to the subject. The irradiation position of the laser light is not particularly limited. The laser light may be radiated from a position other than the probe 11. In the subject, a light absorber absorbs the energy of the radiated laser light and ultrasonic waves (photoacoustic waves) are generated.

The probe 11 includes an ultrasonic wave detector. The probe 11 includes, for example, a plurality of ultrasonic detector elements (ultrasonic transducers) which are one-dimensionally arranged and detects the photoacoustic waves emitted from the subject using the ultrasonic transducers which are one-dimensionally arranged. In addition, the probe 11 may transmit ultrasonic waves to the subject and detect reflected ultrasonic waves of the transmitted ultrasonic waves.

The ultrasonic unit 12 includes a receiving circuit 21, a photoacoustic image generation unit 22, and a control circuit 23. The receiving circuit 21 receives the detected signal of the photoacoustic waves (photoacoustic signal) detected by the probe 11. The photoacoustic image generation unit 22 is a signal processing unit and generates a photoacoustic image on the basis of the received photoacoustic signal. The generation of the photoacoustic image includes, for example, the reconstruction, detection, and logarithmic conversion of the photoacoustic signal. The ultrasonic unit 12 may further include an ultrasonic image generation unit that generates an ultrasonic image on the basis of the detected signal (reflected ultrasonic signal) of the reflected ultrasonic waves detected by the probe 11.

The generation of the image by the ultrasonic unit 12 is not indispensable. The photoacoustic image generation unit 22 may perform any type of signal processing for the photoacoustic signal. In addition, the ultrasonic image generation unit may perform any type of signal processing for the reflected ultrasonic signal.

The control circuit 23 is a control unit and controls each component of the ultrasonic unit 12. In addition, the control circuit 23 transmits a control signal to the laser light source unit 13 or controls, for example, laser emission. Specifically, the control circuit 23 outputs a flash lamp trigger signal, a Q switch trigger signal, and an optical path interruption signal to the laser light source unit 13.

Figure 2:
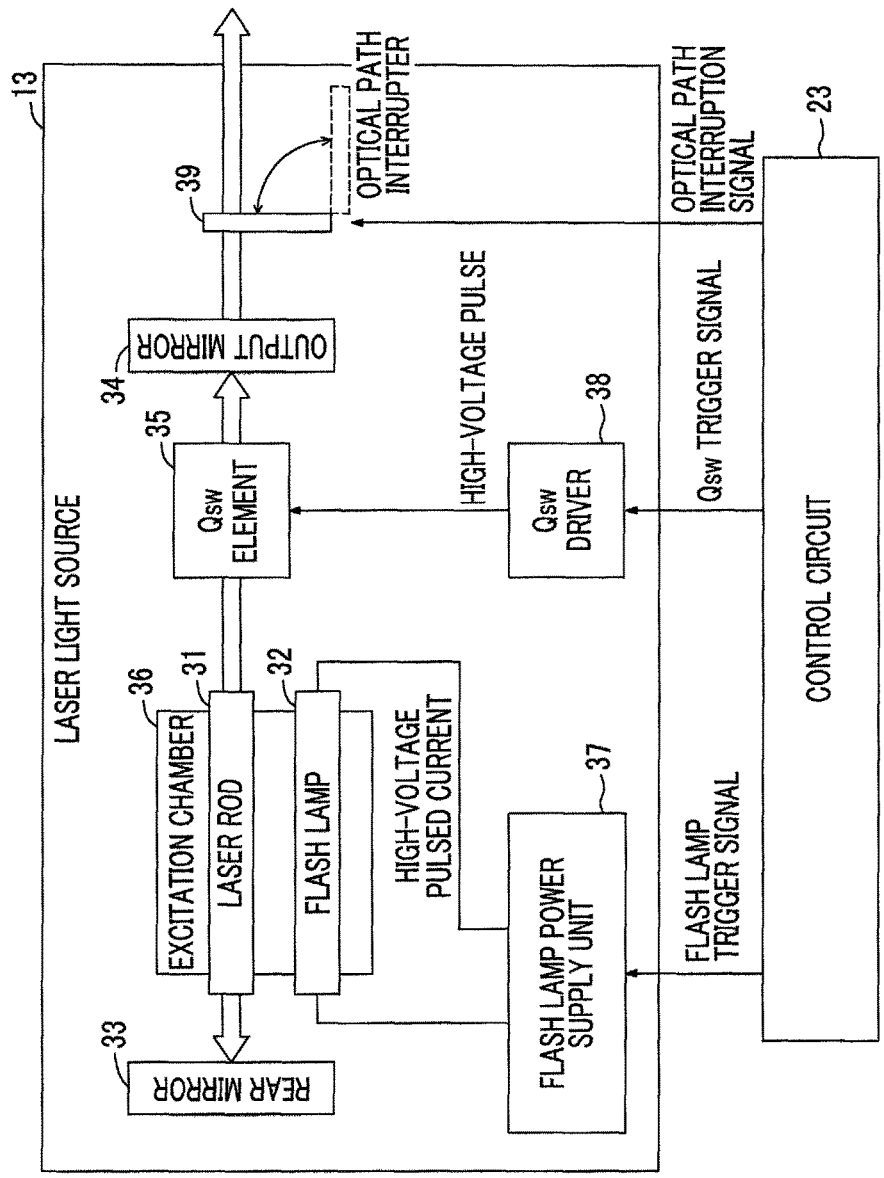
FIG. 2 is a block diagram illustrating the structure of a laser light source unit.

FIG. 2 illustrates the structure of the laser light source unit 13. The laser light source unit 13 includes a laser rod 31, a flash lamp 32, mirrors 33 and 34, a Q switch 35, a flash lamp power supply unit 37, a Q switch driver 38, and an optical path shutter 39. The laser rod 31 is a laser medium. For example, an alexandrite crystal can be used as the laser rod 31. The flash lamp 32 is an excitation unit and emits excitation light to the laser rod 31. The laser rod 31 and the flash lamp 32 are accommodated in the excitation chamber 36. For example, the excitation chamber 36 is provided with a cooling device and the excitation chamber 36 is maintained at a constant temperature.

The mirrors 33 and 34 face each other with the laser rod 31 interposed therebetween. An optical resonator is formed by the mirrors 33 and 34. It is assumed that the mirror 34 is arranged on the output side. The Q switch 35 is inserted into the optical resonator. The Q switch 35 includes, for example, a Pockels cell. For example, Impact10 manufactured by Gooch &. Housego PLC or Q1059 manufactured by Fast Pulse Technology, Inc. can be used as the Q switch 35. The Q switch 35 changes the optical loss of the optical resonator depending on the voltage applied. The Q switch 35 rapidly changes the insertion loss of the optical resonator from a large value (low Q) to a small value (high Q) to obtain pulsed laser light.

The Q switch 35 increases the insertion loss of the optical resonator when a high voltage is applied and decreases the insertion loss of the optical resonator when no voltage is applied. In other words, the optical loss of the optical resonator when a first voltage is applied to the Q switch is more than the optical loss of the optical resonator when a second voltage lower than the first voltage is applied to the Q switch. The first voltage is, for example, about 3 kV and the second voltage is, for example, 0 V (no voltage).

When the first voltage is applied, the Q switch (Pockels cell) 35 causes a predetermined phase difference between a polarized component which is parallel to the optical axis of transmitted light and a polarized component which is perpendicular to the optical axis. The predetermined phase difference is, for example, π/2. In this case, the Q switch 35 functions as a quarter-wave plate for light having the wavelength of laser light. When the second voltage is applied, the Q switch 35 does not cause a phase difference between the polarized component which is parallel to the optical axis of the transmitted light and the polarized component which is perpendicular to the optical axis. That is, the Q switch 35 transmits light, without changing the polarized state. The case in which the first voltage is applied corresponds to the turn-off of the Q switch and the case in which the second voltage is applied corresponds to the turn-on of the Q switch.

The Q switch 35 preferably increases the optical loss of the optical resonator to the extent that laser oscillation does not occur when the first voltage is applied. The invention is not limited to the structure in which, when the first voltage is applied, the Q switch 35 functions as the quarter-wave plate. The Q switch 35 preferably decreases the optical loss of the optical resonator to the extent that laser oscillation occurs when the second voltage is applied. The invention is not limited to the structure in which, when the second voltage is applied, the Q switch 35 transmits light, without changing the polarized state. It is preferable that the Q switch 35 functions as the quarter-wave plate when the first voltage is applied and transmits light, without changing the polarized state, when the second voltage is applied, in order to obtain pulsed laser light with high power and short pulse duration.

The flash lamp power supply unit 37 drives the flash lamp 32. The flash lamp power supply unit 37 applies a voltage between the electrodes of the flash lamp. When receiving the flash lamp trigger signal from the control circuit 23, the flash lamp power supply unit 37 applies a voltage of a few kilovolts to a trigger electrode of the flash lamp 32. When a high voltage is applied to the trigger electrode, the flash lamp 32 emits light.

The Q switch driver 38 applies a high-voltage pulse to the Q switch 35 to control the turn-on and turn-off of the Q switch. The turn-on and turn-off of the Q switch are controlled by the Q switch trigger signal from the control circuit 23.

The optical path shutter 39 is arranged on the optical path of the pulsed laser light emitted from the output-side mirror 34. The optical path shutter 39 is controlled to switch between a closed state in which it blocks the pulsed laser light such that the pulsed laser light is not emitted to the subject and an open state in which it transmits the pulsed laser light such that the pulsed laser light is emitted to the subject. The opening and closing of the optical path shutter 39 are controlled by the optical path interruption signal from the control circuit 23. The optical path shutter 39 may be a mechanical shutter or a combination of a polarizer and an electro-optical element.

Here, the operation mode of the laser light source unit 13 (photoacoustic measurement device 10) includes a first operation mode in which laser light is emitted and a second operation mode in which laser emission is interrupted and the laser emission is waited for. The control circuit 23 opens the optical path shutter 39 in the first operation mode. The control circuit 23 transmits the flash lamp trigger signal to the flash lamp power supply unit 37 to turn on the flash lamp 32. The Q switch driver 38 applies a voltage of about 3 kV to the Q switch 35 to turn off the Q switch 35 before the flash lamp 32 is turned on. After the flash lamp 32 is turned on and the laser rod 31 is sufficiently excited, the control circuit 23 transmits the Q switch trigger signal to the Q switch driver 38. The Q switch driver 38 temporarily reduces the voltage applied to the Q switch 35 to 0 V to change the Q switch 35 from an off state to an on state, in response to the Q switch trigger signal. The insertion loss of the optical resonator is switched from a large value to a small value to generate laser oscillation. Then, pulsed laser light is emitted from the output-side mirror 34.

In the second operation mode, the control circuit 23 closes the optical path shutter 39, using the optical path interruption signal. In addition, the control circuit 23 controls the voltage applied from the Q switch driver 38 to the Q switch 35 such that the voltage is reduced to 0 V, using the Q switch trigger signal. Since the voltage applied to the Q switch 35 is maintained at 0 V, the Q switch 35 is maintained in the on state. In this case, the control circuit 23 periodically transmits the flash lamp trigger signal to the flash lamp power supply unit 37 to maintain the on state of the flash lamp 32. When the flash lamp 32 is turned on, laser oscillation occurs in the optical resonator since the Q switch 35 is in the on state while the flash lamp 32 is turned on. Therefore, laser light with a long pulse which has a longer pulse duration than that when Q switch oscillation is performed is emitted.

The laser light with a long pulse is blocked by the optical path shutter 39 and is not emitted to the subject.

Figure 3:
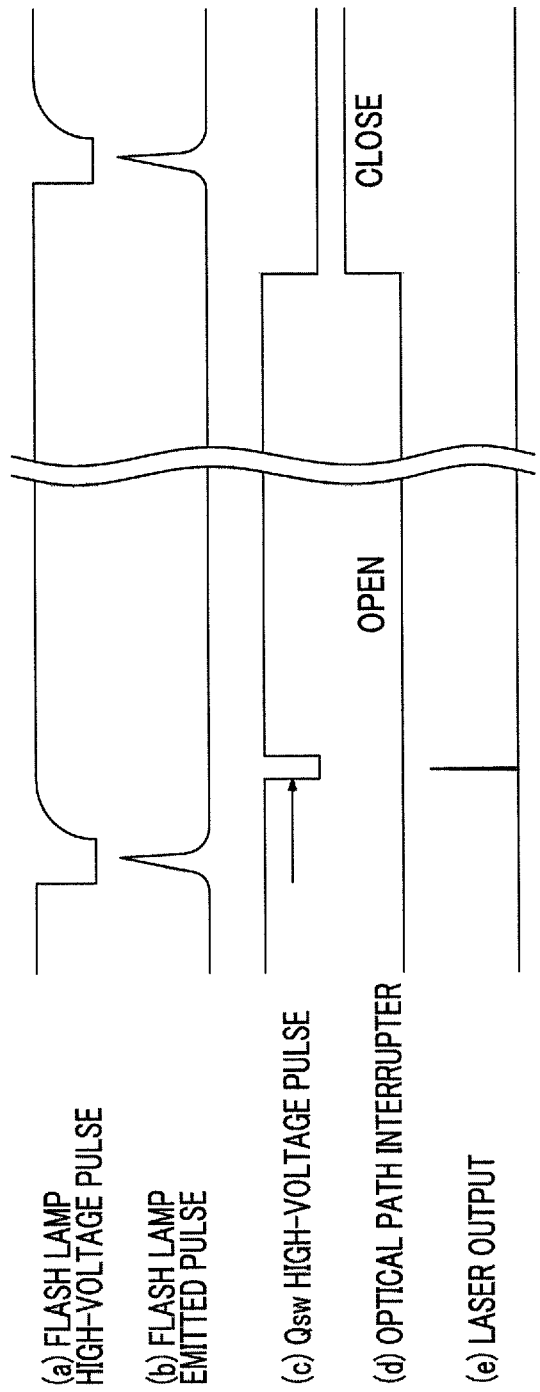
FIG. 3 is a timing chart illustrating the operation waveform of each unit.

FIG. 3 illustrates the operation waveform of each unit. For example, when the doctor operates a console to input an instruction to generate a photoacoustic image (to measure a photoacoustic signal), the laser light source unit 13 operates in the first operation mode. Before the flash lamp 32 emits light, a voltage of about 3 kV is stored in a capacitor of a trigger circuit included in the flash lamp power supply unit 37 (*a*). In addition, a high voltage of about 3 kV is applied to the Q switch 35 and the Q switch is turned off (*c*). The optical path shutter 39 is maintained in the opened state (*d*).

The control circuit 23 outputs the flash lamp trigger signal to the flash lamp power supply unit 37. When receiving the flash lamp trigger signal from the control circuit 23, the flash lamp power supply unit 37 supplies the voltage from the capacitor to the trigger electrode of the flash lamp 32. When a high voltage is applied to the trigger electrode, discharge occurs in the flash lamp 32 and the flash lamp 32 instantaneously emits light (*b*). After the flash lamp 32 emits light, charging to the capacitor of the trigger circuit starts and the capacitor is charged to a voltage of about 3 kV again.

After outputting the flash lamp trigger signal, for example, after a few hundreds of microseconds from the output of the flash lamp trigger signal, the control circuit 23 outputs the Q switch trigger signal to the Q switch driver 38 (*c*). The Q switch driver 38 reduces the voltage applied to the Q switch 35 to 0 V for a predetermined period of time to turn on the Q switch 35, in response to the Q switch trigger signal. When the Q switch 35 is changed from the off state to the on state, energy stored in the optical resonator oscillates at a time and steep pulsed laser light with a pulse duration of about a few nanoseconds to 100 ns is emitted (*e*). After the pulsed laser light is emitted, the Q switch driver 38 returns the voltage applied to the Q switch 35 to 3 kV (*c*) to return the Q switch 35 to the off state.

For example, when the doctor operates the console to input an instruction to stop the generation of the photoacoustic image (the measurement of the photoacoustic signal), the operation mode of the laser light source unit 13 is changed from the first operation mode to the second operation mode. When the operation mode is changed from the first operation mode to the second operation mode, the control circuit 23 closes the optical path shutter 39 using the optical path interruption signal (*d*). In addition, the control circuit 23 switches the voltage applied from the Q switch driver 38 to the Q switch to 0 V, using the Q switch trigger signal (*c*). In the first operation mode, the voltage applied to the Q switch 35 is maintained at 0 V.

The control circuit 23 outputs the flash lamp trigger signal to the flash lamp power supply unit 37. When receiving the flash lamp trigger signal from the control circuit 23, the flash lamp power supply unit 37 supplies the voltage from the capacitor to the trigger electrode of the flash lamp 32. When a high voltage is applied to the trigger electrode, discharge occurs in the flash lamp 32 and the flash lamp 32 instantaneously emits light (*b*). This operation is the same as that in the first operation mode.

When the flash lamp 32 emits light, laser oscillation occurs since the Q switch 35 is in the on state. However, in this case, the laser oscillation is weaker than the Q switch laser oscillation in the first operation mode since it occurs immediately after the laser medium is excited. Laser light with a long pulse which has a longer pulse duration than that in the Q switch laser oscillation is emitted from the output-side mirror 34. The laser light with a long pulse is blocked by the optical path shutter 39 in the closed state and is not output to the outside (e).

In this embodiment, the case in which the first voltage, which is a high voltage, is applied to the Q switch corresponds to the turn-off of the Q switch and the case in which the second voltage, which is a low voltage, is applied to the Q switch corresponds to the turn-on of the Q switch. According to this structure, it is not necessary to provide the quarter-wave plate which needs to be provided in the optical resonator when the case in which a high voltage is applied to the Q switch corresponds to the turn-on of the Q switch and the case in which a low voltage (0 V) is applied to the Q switch corresponds to the turn-off of the Q switch. Therefore, it is possible to simplify the internal structure of the optical resonator.

In this embodiment, in the second operation mode in which laser emission is not performed and the laser emission is waited for, the optical path shutter 39 is in the closed state and the voltage applied to the Q switch 35 is controlled to be the second voltage which is a low voltage. When the second voltage is applied, the Q switch 35 is turned on and the flash lamp 32 emits light. Then, in the optical resonator, laser oscillation occurs. However, the laser light is blocked by the optical path shutter 39 and is not emitted to the outside. Therefore, it is not necessary to stop the excitation of the laser medium by the flash lamp 32. In this embodiment, in the second operation mode, the voltage applied to the Q switch is switched to the second voltage which is a low voltage. Therefore, in the standby mode, it is possible to prevent a high voltage from being continuously applied to the Q switch and to prevent deterioration of the Q switch.

Figure 4:
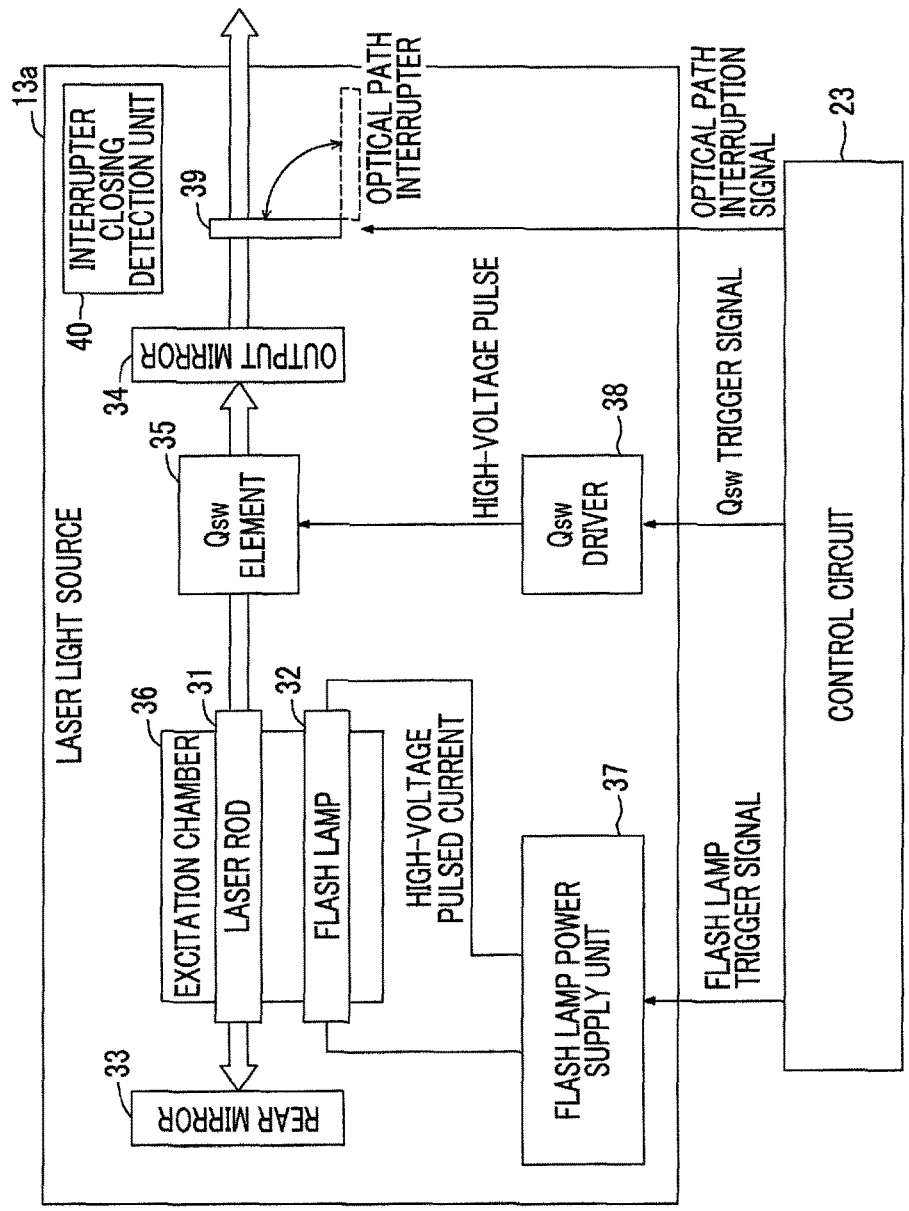
FIG. 4 is a block diagram illustrating a laser light source unit of a photoacoustic measurement device according to a second embodiment of the invention.

Next, a second embodiment of the invention will be described. FIG. 4 illustrates a laser light source unit of a photoacoustic measurement device according to the second embodiment of the invention. A laser light source unit 13a according to this embodiment includes an interrupter closing detector 40 in addition to the structure of the laser light source unit 13 according to the first embodiment illustrated in FIG. 2. The interrupter closing detector 40 detects the closing of the optical path shutter 39.

When the interrupter closing detector 40 detects that the optical path shutter 39 is closed, the laser light source unit 13a operates in the second operation mode. Specifically, for example, the control circuit 23 closes the optical path shutter 39 using the optical path interruption signal. After the interrupter closing detector 40 detects that the optical path shutter 39 is closed, the control circuit 23 changes the voltage applied to the Q switch 35 to 0 V, using the Q switch trigger signal. According to this structure, before the optical path shutter 39 is closed, the voltage applied to the Q switch 35 is changed to 0 V. Therefore, it is possible to prevent the flash lamp 32 from being turned on and thus to prevent laser light with a long pulse from being emitted to the outside. As a result, it is possible to improve safety.

For example, when the doctor operates the console to input an instruction to stop the generation of a photoacoustic image, the control circuit 23 closes the optical path shutter 39 in order to change the operation mode to the second operation mode. After the closing of the optical path shutter 39 is detected, the control circuit 23 controls the voltage applied to the Q switch 35 to be 0 V. Alternatively, for example, after the doctor operates the console to input an instruction to close the optical path shutter 39 and the closing of the optical path shutter 39 is detected, the control circuit 23 may control the voltage applied to the Q switch 35 to be 0 V, thereby changing the operation mode to the second operation mode.

In FIG. 2, the flash lamp 32 is used as the excitation unit. However, the excitation unit is not limited to the flash lamp 32. Light sources other than the flash lamp 32 may be used as the excitation light source. In FIG. 2, a wavelength selection unit for controlling an oscillation wavelength may be inserted into the optical resonator and the laser light source unit 13 may be a variable-wavelength laser which switches light components with a plurality of wavelengths and emits the light component.

In the above-described embodiments, for example, when the doctor stops the generation of the photoacoustic image, the laser light source unit 132 operates in the second operation mode. However, the invention is not limited thereto. For example, the ultrasonic unit 12 may have three operation modes for generating images, that is, an operation mode for generating only an ultrasonic image, an operation mode for generating only a photoacoustic image, and an operation mode for generating both a photoacoustic image and an ultrasonic image. When the ultrasonic unit 12 operates in the operation mode in which no photoacoustic image is included in a generated image, the laser light source unit 13 may operate in the second operation mode. Alternatively, for example, when the probe 11 or the console of the ultrasonic unit 12 is not operated for a predetermined period of time or more, the laser light source unit 13 may operate in the second operation mode.

The preferred embodiments of the invention have been described above. However, the photoacoustic measurement device and the laser light source according to the invention are not limited only to the above-described embodiments and various modifications and changes of the structures according to the above-described embodiments are also included in the scope of the invention.

The invention claimed is:

1. A photoacoustic measurement device comprising:
    a laser medium;
    an excitation unit that excites the laser medium;
    an optical resonator including a pair of mirrors that face each other with the laser medium interposed therebetween;
    a Q switch that is provided on an optical path of the optical resonator and changes optical loss of the optical resonator, according to a voltage applied, such that the optical loss of the optical resonator when a first voltage level is applied to the Q switch is more than the optical loss of the optical resonator when a second voltage level lower than the first voltage level is applied to the Q switch;
    a laser light source that is provided on an optical path of laser emission light and has an optical path shutter;
    an acoustic wave detection unit that, after light is emitted from the laser light source to a subject, detects a photoacoustic wave generated by the emission of the light;
    a photoacoustic signal processing unit that performs signal processing for the photoacoustic wave; and
    a control unit that performs control such that, in a first operation mode in which laser emission is performed, the optical path shutter transmits the light from the laser light source and the voltage applied to the Q switch is changed from the first voltage level to the second voltage level to emit pulsed laser light after the excitation unit excites the laser medium; and such that, in a second operation mode in which the laser emission is interrupted and waited for, the optical path shutter blocks the light from the laser light source and the second voltage level is applied to the Q switch.

2. The photoacoustic measurement device according to claim 1,
wherein, in a case in which the first operation mode is switched to the second operation mode, the control unit closes the optical path shutter and changes the voltage applied to the Q switch from the first voltage level to the second voltage level.

3. The photoacoustic measurement device according to claim 2,
wherein, in the second operation mode, the excitation unit periodically excites the laser medium.

4. The photoacoustic measurement device according to claim 3,
wherein the Q switch gives a predetermined phase difference between a polarized component which is parallel to an optical axis of transmitted light and a polarized component which is perpendicular to the optical axis when the first voltage level is applied and does not give a phase difference between the polarized component which is parallel to the optical axis of the transmitted light and the polarized component which is perpendicular to the optical axis when the second voltage level is applied.

5. The photoacoustic measurement device according to claim 3,
wherein the Q switch functions as a quarter-wave plate for light with a wavelength of laser light when the first voltage level is applied.

6. The photoacoustic measurement device according to claim 2, wherein the second voltage level is 0 V.

7. The photoacoustic measurement device according to claim 2,
wherein the Q switch gives a predetermined phase difference between a polarized component which is parallel to an optical axis of transmitted light and a polarized component which is perpendicular to the optical axis when the first voltage level is applied and does not give a phase difference between the polarized component which is parallel to the optical axis of the transmitted light and the polarized component which is perpendicular to the optical axis when the second voltage level is applied.

8. The photoacoustic measurement device according to claim 2,
wherein the Q switch functions as a quarter-wave plate for light with a wavelength of laser light when the first voltage level is applied.

9. The photoacoustic measurement device according to claim 1,
wherein, in the second operation mode, the excitation unit periodically excites the laser medium.

10. The photoacoustic measurement device according to claim 9,
wherein the second voltage level is 0 V.

11. The photoacoustic measurement device according to claim 9,
wherein the Q switch gives a predetermined phase difference between a polarized component which is parallel to an optical axis of transmitted light and a polarized component which is perpendicular to the optical axis when the first voltage level is applied and does not give a phase difference between the polarized component which is parallel to the optical axis of the transmitted light and the polarized component which is perpendicular to the optical axis when the second voltage level is applied.

12. The photoacoustic measurement device according to claim 9,
wherein the Q switch functions as a quarter-wave plate for light with a wavelength of laser light when the first voltage level is applied.

13. The photoacoustic measurement device according to claim 1,
wherein the second voltage level is 0 V.

14. The photoacoustic measurement device according to claim 1,
wherein the Q switch gives a predetermined phase difference between a polarized component which is parallel to an optical axis of transmitted light and a polarized component which is perpendicular to the optical axis when the first voltage level is applied and does not give a phase difference between the polarized component which is parallel to the optical axis of the transmitted light and the polarized component which is perpendicular to the optical axis when the second voltage level is applied.

15. The photoacoustic measurement device according to claim 1,
wherein the Q switch functions as a quarter-wave plate for light with a wavelength of laser light when the first voltage level is applied.

16. The photoacoustic measurement device according to claim 1,
wherein the photoacoustic signal processing unit generates a photoacoustic image on the basis of the photoacoustic signal.

17. The photoacoustic measurement device according to claim 1,
wherein the laser light source further includes an interrupter closing detector that detects the closing of the optical path shutter, and
when the interrupter closing detector detects that the optical path shutter is closed, the control unit controls the voltage applied to the Q switch to be the second voltage level.

18. The photoacoustic measurement device according to claim 1,
wherein the photoacoustic measurement device operates in the first operation mode when an instruction to measure the photoacoustic signal is input and operates in the second operation mode when an instruction to stop the measurement of the photoacoustic signal is input.

19. The photoacoustic measurement device according to claim 1,
wherein, in the first operation mode, after changing the voltage applied to the Q switch from the first voltage level to the second voltage level, the control unit performs control such that the first voltage level is applied to the Q switch.

20. A laser light source for use in the photoacoustic measurement device of claim 1, comprising:
a laser medium;
an excitation unit that excites the laser medium;
an optical resonator including a pair of mirrors that face each other with the laser medium interposed therebetween;
a Q switch that is provided on an optical path of the optical resonator and changes optical loss of the optical resonator, according to a voltage applied, such that the optical loss of the optical resonator when a first voltage level is applied to the Q switch is more than the optical loss of the optical resonator when a second voltage level lower than the first voltage level is applied to the Q switch; and an optical path shutter that is provided on an optical path of laser emission light, wherein, in a first operation mode in which laser emission is performed, the optical path shutter transmits the light from the laser light source and the voltage applied to the Q switch is changed from the first voltage level to the second voltage level to emit pulsed laser light after the excitation unit excites the laser medium, and in a second operation mode in which the laser emission is interrupted and waited for, the optical path shutter blocks the light from the laser light source and the second voltage level is applied to the Q switch.

* * * * *